US007644715B2

(12) United States Patent
Hayes et al.

(10) Patent No.: US 7,644,715 B2
(45) Date of Patent: Jan. 12, 2010

(54) RESTLESS LEG SYNDROME TREATMENT

(75) Inventors: Clint Hayes, Roseville, CA (US); David R. Hennings, Roseville, CA (US); John R. Kingsley, Roseville, CA (US); Don Johnson, Roseville, CA (US)

(73) Assignee: CoolTouch, Incorporated, Roseville, CA (US)

( * ) Notice: Subject to any disclaimer, the term of this patent is extended or adjusted under 35 U.S.C. 154(b) by 3 days.

(21) Appl. No.: 11/855,762

(22) Filed: Sep. 14, 2007

(65) Prior Publication Data

US 2008/0071333 A1    Mar. 20, 2008

Related U.S. Application Data

(63) Continuation-in-part of application No. 10/982,504, filed on Nov. 4, 2004, now Pat. No. 7,524,316, which is a continuation-in-part of application No. PCT/US03/35178, filed on Oct. 30, 2003, application No. 11/855,762, which is a continuation-in-part of application No. 10/699,212, filed on Oct. 30, 2003.

(60) Provisional application No. 60/825,687, filed on Sep. 14, 2006, provisional application No. 60/422,566, filed on Oct. 31, 2002.

(51) Int. Cl.
*A61B 19/00* (2006.01)

(52) U.S. Cl. .......................... 128/898; 606/15; 607/89; 607/101

(58) Field of Classification Search ...................... 606/7, 606/14–16, 32, 49; 607/88, 89, 92, 96–101, 607/115, 116; 128/898
See application file for complete search history.

(56) References Cited

U.S. PATENT DOCUMENTS

| 6,797,259 | B2 * | 9/2004 | Rabinowitz et al. ........... 424/45 |
| 6,981,971 | B2 * | 1/2006 | Caldera et al. ................ 606/15 |
| 7,153,298 | B1 * | 12/2006 | Cohen ......................... 606/12 |
| 7,273,478 | B2 * | 9/2007 | Appling et al. ............... 606/15 |
| 2003/0176822 | A1 * | 9/2003 | Morgenlander .............. 601/152 |
| 2004/0092913 | A1 * | 5/2004 | Hennings et al. ............... 606/3 |
| 2005/0131400 | A1 * | 6/2005 | Hennings et al. ............. 606/15 |
| 2007/0123846 | A1 * | 5/2007 | Hennings ..................... 606/15 |
| 2008/0021527 | A1 * | 1/2008 | Hennings et al. ............. 607/89 |

* cited by examiner

*Primary Examiner*—Ahmed M Farah
(74) *Attorney, Agent, or Firm*—Ray K. Shahani, Esq.; Kin Hung Lai

(57) ABSTRACT

The present invention describes a method of treating restless leg syndrome by eliminating venous reflux in an underlying vein. The malfunctioning vein can be removed or ablated by inserting a catheter into the vein that transmits sufficient energy to coagulate or ablate the lining of the vein causing it to permanently close, eliminating the source of venous reflux and the symptom of restless leg syndrome.

4 Claims, 7 Drawing Sheets

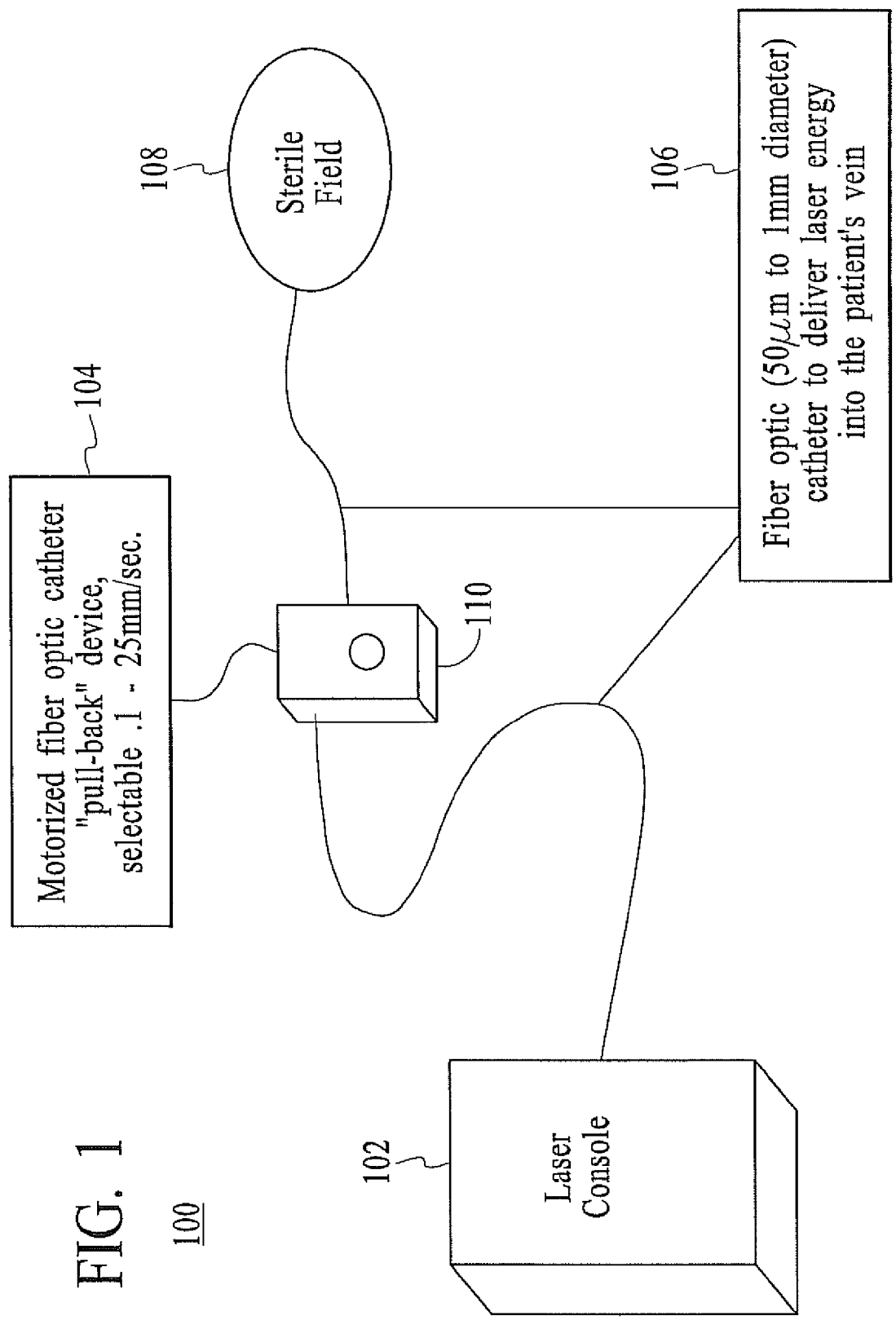

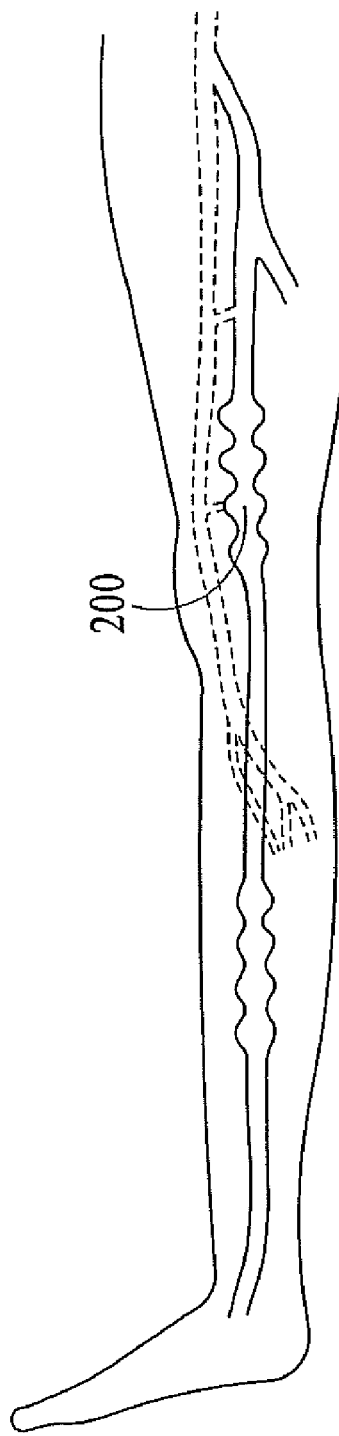
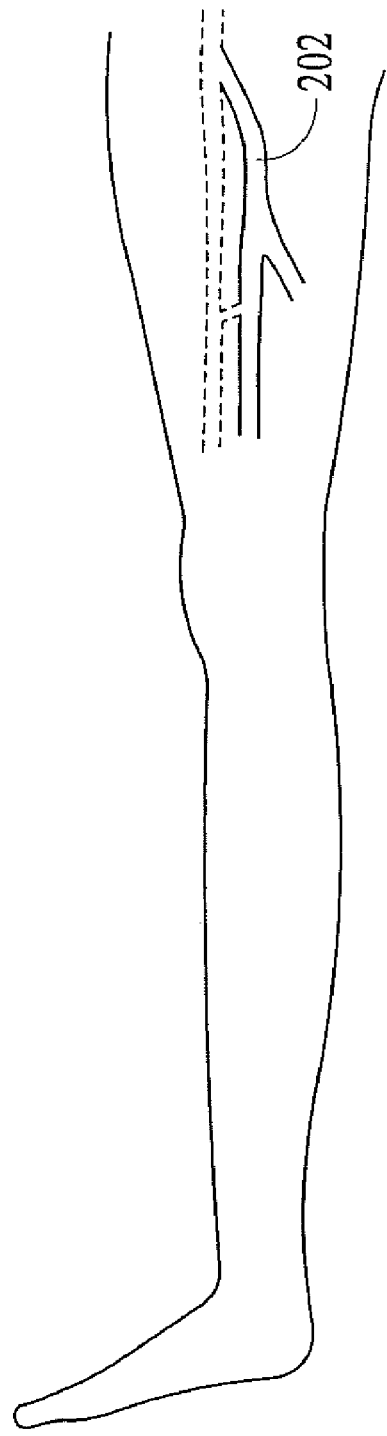
FIG. 2A
FIG. 2B

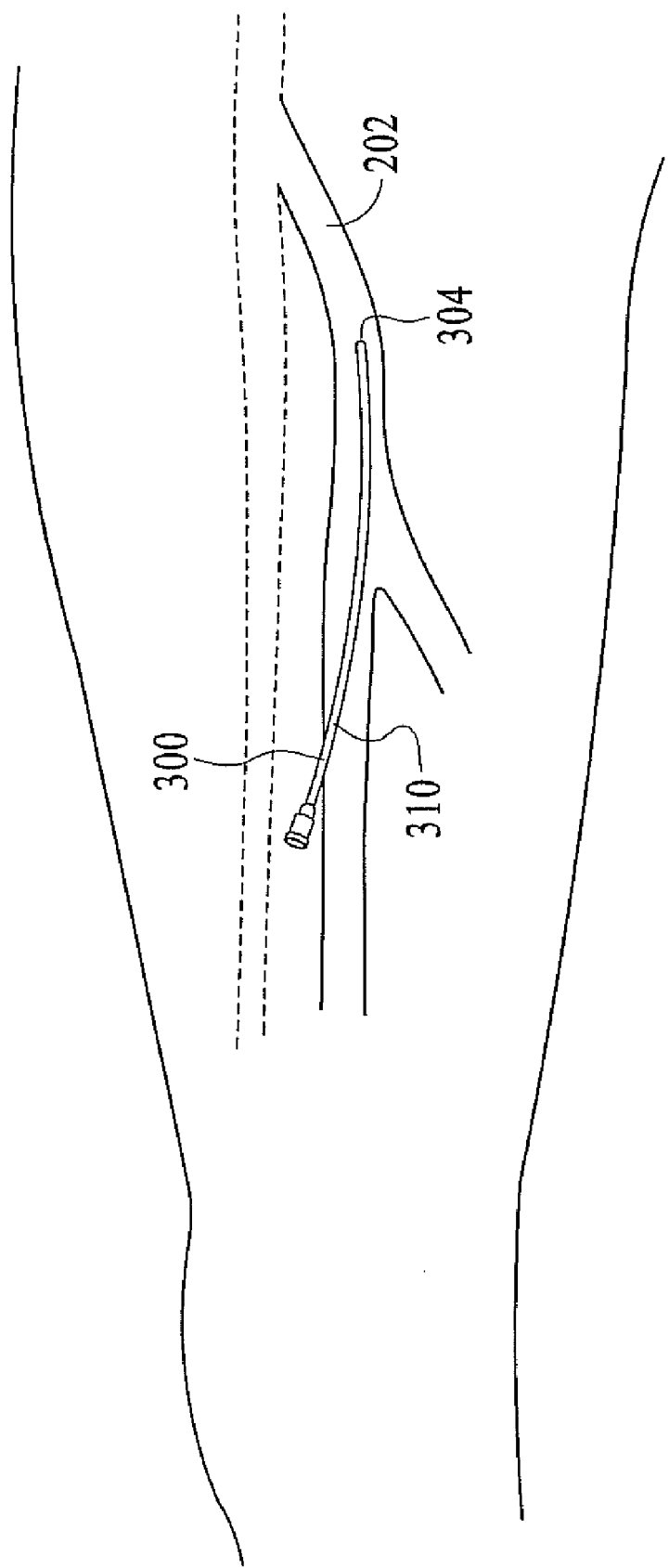

RESTLESS LEG SYNDROME TREATMENT

RELATED APPLICATIONS

This Application is related to pending U.S. Provisional Patent Application Ser. No. 60/825,687 filed Sep. 14, 2006 entitled RESTLESS LEG SYNDROME TREATMENT. This application is also a continuation-in-part of and claims benefits of U.S. patent application Ser. No. 10/982,504, filed on Nov. 4, 2004, and titled "ENDOVENOUS CLOSURE OF VARICOSE VEINS WITH MID INFRARED LASER", which application is a continuation-in-part of and claims the benefit of International Application Number PCT/US2003/035178, filed under the Patent Cooperation Treaty on Oct. 30, 2003, titled "ENDOVENOUS CLOSURE OF VARICOSE VEINS WITH MID INFRARED LASER", which application claims the benefit of U.S. Provisional Patent Application Ser. No. 60/422,566 filed Oct. 31, 2002, entitled "ENDOVENOUS CLOSURE OF VARICOSE VEINS WITH MID INFRARED LASER", each of which applications is incorporated herein by reference in its entirety and claims any and all benefits to which it is entitled therefrom. This Application is also a continuation-in-part of U.S. application Ser. No. 10/699,212 filed Oct. 30, 2003, entitled "ENDOVENOUS CLOSURE OF VARICOSE VEINS WITH MID INFRARED LASER", which application claims the benefit of U.S. Provisional Patent Application Ser. No. 60/422,566 filed Oct. 31, 2002, entitled "ENDO VENOUS CLOSURE OF VARICOSE VEINS WITH MID INFRARED LASER", each of which applications is incorporated herein by reference in its entirety.

FIELD OF THE INVENTION

This invention relates to methods and apparatus for treating restless leg syndrome (RLS). Specifically the method includes eliminating venous reflux in a vein in the leg by closing it with energy derived from a radio frequency generator, using a foam sclerosant, and using an electrical resistance circuit or a laser.

BACKGROUND OF THE INVENTION

RLS is a poorly understood disorder in which patients experience compelling urges to move the legs usually accompanied by intense, unpleasant sensations in their legs. RLS affects 5-15% of the American and European populations. RLS affects the general population with a mean age at onset of 27.2 years. Onset of RLS is often before age 20 in 38.3% of patients. Women are twice as likely to be affected. The earliest description of an RLS case was by English physician and anatomist Sir Thomas Willis in 1672. RLS lingered in anonymity until 1944, when Swedish neurologist Karl Ekbom first described the salient features. In 1945 he coined the phrase "restless legs". The addition of the word "syndrome" designates this malady as a condition defined by clinical symptoms rather than by any specific pathological process.

Most patients find they cannot describe the nature of their sensations. It is frequently unrecognized or misdiagnosed and therefore widely undertreated. Dr. Ekbom felt that "this is evidently due to the fact that the sensations do not resemble any known phenomenon that can be used as a comparison." They are variably described as heebie-jeebies, antsy, Jimmy legs, or as creeping-crawling, pulling, drawing, boring, wormy, etc. The sensations are painful in about 30% of patients. Patients experience intense unpleasant sensations deep in the legs that are accompanied by an irresistible urge to move the affected limbs. The sensations are usually located in the calf area, but may be felt anywhere from the ankles to the thighs. The arms are rarely involved.

There is a wide variation in severity with some patients experiencing only occasional mild symptoms, while others struggle with disabling episodes on a nightly basis. Symptoms of RLS are worse in the evening and during periods of relaxation or decreased activity, especially while lying down or reclining. Patients are often completely asymptomatic in the morning. The reason for this is unknown. The desire to relieve the symptoms can lead to a compulsion involving excessive limb movements. The sensations and the compulsion to relieve them frequently become terribly distressing. As RLS symptoms are stronger at bedtime, sleep-onset insomnia is common. RLS sufferers often find they cannot sleep until the early morning hours. Patients with severe RLS experience nightly attacks that lead to chronic sleep-deprivation with its accompanying psychological and cognitive deficits.

Investigators have made great strides in the understanding and treatment of RLS over the last two decades, to the nightly relief of millions of victims. The etiology of RLS remains elusive, however, and a final common pathway has yet to be described. According to Dr M. J. Thorpy, primary RLS "may represent a heterogeneous group of disorders because no single pathophysiologic mechanism explains all the clinical features exhibited."

There are no classic physical findings, no conclusive blood assays, and no standard radiological or sleep studies to diagnose RLS. Because there is no known biomarker, the diagnosis of RLS can only be made based on clinical history. In an attempt to more clearly define RLS, the IRLSSG developed RLS diagnostic criteria in 1995. An IRLSSG consensus panel at the National Institutes of Health (NIH) modified these criteria to their present form in 2003. These four criteria are necessary and sufficient for the diagnosis of RLS. They include: 1) Urges to move the limbs with or without unpleasant sensations, 2) worsening of symptoms at rest, 3) improvement of symptoms with movement, and 4) worsening of symptoms at night. The IRLS questionnaire (FIG. 1) was developed by the IRLSSG and validated in 2003 as a consistent, reliable tool to objectively measure RLS severity.

RLS is divided into primary (idiopathic) and secondary causes. Primary RLS is felt to be the most common form and is suspected to be a sensorimotor abnormality associated with central nervous system dysfunction involving abnormal brain iron metabolism and irregularity of central dopaminergic neurotransmitter pathways. Primary RLS likely represents a heterogenous group because no single pathophysiologic mechanism explains all the clinical features exhibited. Secondary RLS occurs in such disparate conditions as back pain, iron deficiency, renal failure, pregnancy, neuropathy, and venous disease. Various medications are known to precipitate RLS attacks. The fact that RLS is a "mixed bag" diagnosis has complicated research, confounded investigators, and frustrated clinicians; in that various medications work in only a percentage of affected patients. Current treatment therefore focuses on nightly management of symptoms rather than on cure.

In 1995, Dr. A. H. Kanter's groundbreaking study suggested that sclerotherapy in patients with varicose veins and RLS is 98% effective in initial relief of RLS. This is the first article to describe operative treatment of RLS. Dr Kanter concluded that all RLS patients with varicose veins should be considered for phlebological evaluation and possible treatment before being consigned to chronic drug therapy.

Secondary RLS is known to occur in and is secondary to such disparate conditions as iron deficiency, renal failure, pregnancy, neuropathy, and venous insufficiency. Various medications are known to exacerbate existing RLS, even precipitate RLS, and other causes are likely.

Because RLS is a "mixed bag" diagnosis, research investigators have been confounded when treatments only work on a portion of the test subjects. Treatment of the secondary causes of RLS can frequently cure patients of this distressing malady. Because venous insufficiency is a secondary cause, treatment of this cause may cure the patient of RLS.

Venous insufficiency is quite common, affecting 10-15% of adult men and 20-25% of adult women. Duplex ultrasound studies reveal that saphenous vein reflux is the most common form of venous insufficiency and is the underlying condition in most patients suffering with varicose veins. Sclerotherapy in patients with varicose veins and RLS has been shown to be 98% effective in initial relief of RLS with recurrence rate of 8% and 28% at one and two years, respectively. Sclerotherapy is not a very effective treatment for varicose veins. While effective for tiny surface veins, the injection of liquid sclerosant into the large veins responsible for venous insufficiency has a low success rate. This method requires multiple injections, can be very painful, and the veins often reopen in a few years requiring, continual treatments. Most RLS patients are not willing to undergo this therapy. Although prior art consists of drug therapy and occasionally the use of compression stockings, surgery in the form of vein stripping has also not been considered a treatment for this condition because of the significant morbidity associated with the procedure. This invention discloses the use of a new minimally invasive treatment for venous insufficiency that is benign enough to be considered as a treatment and a cure for RLS with a significantly improved benefit to cost ratio.

Varicose veins have been treated in a similar manner except that the clinical symptoms of varicose veins are much more evident. Bulging veins, ulcers, pain and leg tiredness are all symptoms of varicose vein disease. This invention also relates to otherwise healthy legs that do not necessarily show these symptoms but rather an early stage of venous disease that causes RLS without bulging and painful varicose veins.

This connection between venous insufficiency and restless leg syndrome has been noted in the literature but the root cause of the disease and the connections to the venous system is not obvious. It was only through anecdotal comments by patients who had restless leg syndrome and were also successfully treated for varicose veins that the connection became clear. The restless leg symptoms disappeared after treatment for varicose Veins. This invention takes this one step farther and claims that restless legs can be successfully treated even without the symptoms of varicose veins by eliminating venous reflux in a segment adjacent to the twitching or skin movement.

ADVANTAGES AND SUMMARY OF THE INVENTION

This invention describes a method to cure Restless Legs Syndrome (RLS) in a percentage of patients without the expense and pain associated with surgery and with far better short and long term results than the use of liquid sclerotherapy. This new method promises to become the treatment of choice to enable RLS patients to be taken off of debilitating and expensive drug therapy that only treats the symptoms of RLS.

It is an advantage of the present invention to provide a method of treating restless leg syndrome in which the method comprises the step of eliminating reflux from an underlying vein. It is a further advantage of the present invention to provide said method in which the step of eliminating reflux from an underlying vein comprises closing an underlying leg vein with energy to eliminate venous reflux. In an embodiment of the present invention, the energy is of the type selected from the group consisting of infrared, ultraviolet, visible, radio frequency, ultrasound and laser. In an embodiment of the present invention, the step of eliminating reflux from an underlying vein comprises using an endovenous catheter to deliver energy to a segment of incompetent vein. In an embodiment of the present invention, step of eliminating reflux from an underlying vein comprises uses foam sclerotherapy.

It is an advantage of the present invention to provide a method of treating restless leg syndrome wherein the step of using laser energy to eliminate reflux in a short segment of vein around the symptomatic region.

It is yet another advantage of the present invention to provide a method of treating restless leg syndrome comprising the step of eliminating venous reflux in an underlying vein in the absence of vein varicosities, ulcers or other visible symptoms.

It is yet another advantage of the present invention to provide an endovenous method of treating restless leg syndrome comprising the step of using a laser having a wavelength between about 1.2 and about 2.7 um to heat and shrink collagen in a vessel wall, and in which the step of delivering the laser energy with a fiber optic laser delivery device. An embodiment of the invention comprises the steps of inserting a fiber optic laser delivery device into the vein and using a pullback device to retract the fiber optic laser delivery device through the vein at a rate of between about 0.1 mm/sec and about 10.0 mm/sec while simultaneously delivering laser energy therefrom. In an embodiment of the invention, the fiber optic laser delivery device is retracted at a rate of between about 0.5 mm/sec and about 5.0 mm/sec. In another embodiment of the invention, the pullback device is left off initially to let heat build up at the start therefore enabling a better closure of the vessel. It is an advantage to remove blood from the vein prior to treatment with laser energy. It is yet a further advantage to introduce the fiber optic laser delivery device to the vein through an introducer catheter. In an embodiment of the present invention, a pulsed laser is used, the pulse width between 1 and 5000 microseconds.

Further details, objects and advantages of the present invention will be come apparent through the following descriptions, and will be included and incorporated herein.

BRIEF DESCRIPTION OF THE DRAWINGS

FIG. 1 is a representative schematic block diagram of an embodiment of an apparatus 100 of the present invention for performing of a varicose vein closure procedure of the present invention.

FIG. 2A is a representative view of varicosed veins 200 to be treated according to the method and apparatus of the present invention.

FIG. 2B is a representative view of the GSV 202 to be treated according to the method and apparatus of the present invention.

FIG. 3A is a representative view showing the beginning of the introducer or dilator 300 for percutaneous access according to the method and apparatus of the present invention.

DETAILED DESCRIPTION OF

Figure 3B:
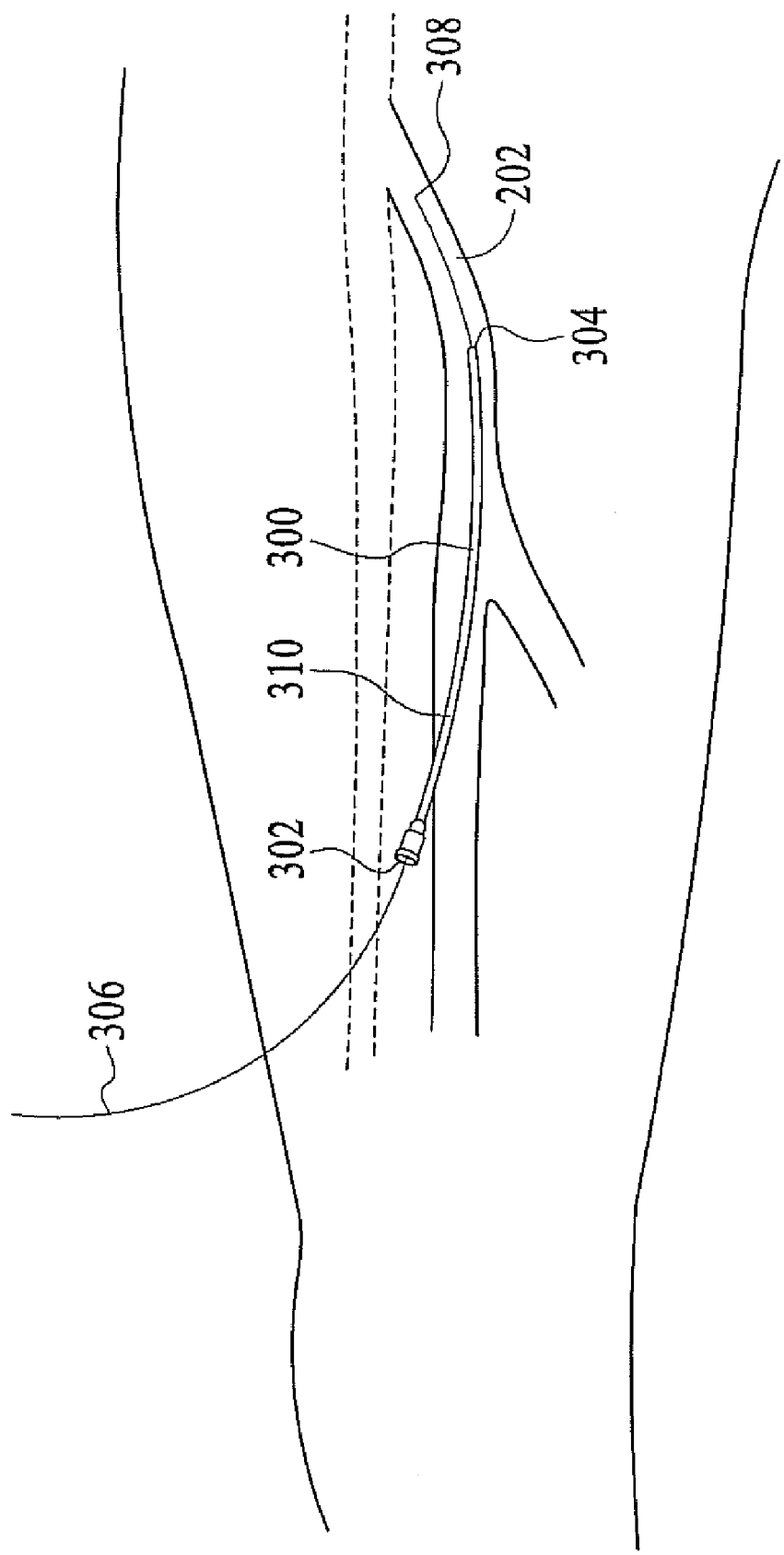
FIG. 3B is a representative view showing the use of the introducer or dilator 300 with the laser fiber 306 passing through the lumen 302 of the dilator 300 and into the GSV 202 according to the method and apparatus of the present invention.

1. Perform and document a thorough exam of all veins contributing to vascular insufficiency and reflux.
2. Obtain percutaneous access of the vessel being treated using a Seldinger Technique. The length and size access devices will vary depending on the length and size of vein being treated and the fiber selected.
3. Advance catheter
    Advance the catheter through the introducer sheath until it is approximately 1-2 cm below the saphenofemoral junction (SFJ) or the saphenopopliteal junction (SPJ) or at the appropriate distance based on the junction or vein being treated.
    Confirm position of the catheter tip with ultrasound.
    Visualize the aiming beam through the patient's skin (the room lights may need to be darkened at this point for adequate visualization).
4. Once the catheter is in the desired position, the following methods should be used to reduce vein size:
    Position patient in 20°-30° Trendelenburg or equivalent. It will be understood that this typically refers to a supine position with the patient inclined at an angle of 0-45 degrees, so that the pelvis is higher than the head, used during and after operations in the pelvis or for shock.
    Elevate the extremity being treated
    Use a syringe to suction vein contents through the access device port
    Use a compression wrap
    Manual compression
5. Inject local anesthesia around the vein being treated
    Using ultrasound, observe infiltration of tumescent anesthesia solution around the vein.
    The vein should be completely surrounded with at least 10 mm of fluid to provide thermal protection for the surrounding tissue.
6. Remove or pull out any introducer sheath, leaving just the proximal tip just at the skin edge of the access site
    Removal of the sheath will prevent the catheter from entering the sheath during the automatic pull-back.
    Reconfirm tip position once the sheath has been pulled out.
7. Begin treatment and observe tissue response under ultrasound observation. If the desired tissue effect in the vein is not seen, increase wattage. Indications of adequate tissue response include:
    Slowing or stopping of forward movement of flow
    Thickening of the vein wall
    Contraction of the vein
    Decrease in size of the vein lumen
8. Continue to observe the aiming beam through the skin and the tissue effect in the vein with the ultrasound. Place fingers on either side of the catheter at the exit point from the skin to verify movement and to support the fiber as it is being pulled out.
9. Following the treatment, observe the appearance of the vein with the ultrasound:
    Vein appears more dense and thickened (more echogenic)
    Vein is less compressible with pressure from the ultrasound probe
    Vein lumen is noticeably smaller in size
    Vein does not demonstrate spontaneous flow
10. Apply dressings at the completion of the procedure:
    Steri-Strips®
    Absorbent dressing over access site
    3-inch self-adherent tape wrap
    30-40 mm Hg compression hosiery should be placed over dressings with the patient lying down.

Devices and Equipment:

As described above, the tissue may be heated or treated with any operative heating device. These include, but are not limited to the followings: a laser diode or other laser source, electrical current, radiofrequency waves, microwaves, ultrasound or other source of electromagnetic energy which penetrates into regions of tissue, by conduction or convection as with bubble generation in blood, contact device, active or passive heating means, etc., thus preferentially heating a region of tissue without excessive or otherwise undesirable heating of or effect on surrounding tissue.

Examination of veins and diagnosis of RLS is taught by Allen R P, Abetz L, Washburn T, Early C J. THE IMPACT OF RESTLESS LEGS SYNDROME (RLS) ON SLEEP AND COGNITIVE FUNCTION. Eur J Neurol. 2002; 9(suppl2): 50, which is hereby incorporated herein by reference in its entirety, without limitations.

Use of ultrasound for intravenous catheter or other structure visualization, catheter positioning and treatment device, structure and function is further taught by U.S. Pat. No. 6,024, 703 filed May 7, 1997 entitled ULTRASOUND DEVICE FOR AXIAL RANGING, which is hereby incorporated herein by reference in its entirety, without limitations.

Percutaneous access of vessels methods, device, structure and function is further taught by pending U.S. patent application Ser. No. 10/699,212 filed Oct. 30, 2003 entitled ENDOVENOUS CLOSURE OF VARICOSE VEINS WITH MID INFRARED LASER, which is hereby incorporated herein by reference in its entirety, without limitations.

Automatic, motorized or other equivalent pull-back method, device, structure and function is further taught by pending U.S. patent application Ser. No. 10/699,212 filed Oct. 30, 2003 entitled ENDOVENOUS CLOSURE OF VARICOSE VEINS WITH MID INFRARED LASER, which is hereby incorporated herein by reference in its entirety, without limitations.

FIG. 1 is a representative schematic block diagram of the apparatus 100 of the present invention for performing the varicose vein closure procedure of the present invention. As shown, the system 100 of the present invention includes a laser console 102, a motorized, fiber optic catheter "pull-back" machine 104, a fiber optic catheter or other laser delivery device 106 to deliver laser energy into the patient's vein, a sterile field 108 and a controller 110.

FIG. 2A is a representative view of varicosed veins 200 to be treated according to the method and apparatus of the present invention. FIG. 2B is a representative view of the GSV 202 to be treated according to the method and apparatus of the present invention. FIG. 3A is a representative view showing the beginning of the introducer or dilator 300 for percutaneous access according to the method and apparatus of the present invention. FIG. 3B is a representative view showing the use of the introducer or dilator 300 with the laser fiber 306 passing through the lumen 302 of the dilator 300 and into the GSV 202 according to the method and apparatus of the present invention.

Figure 4:
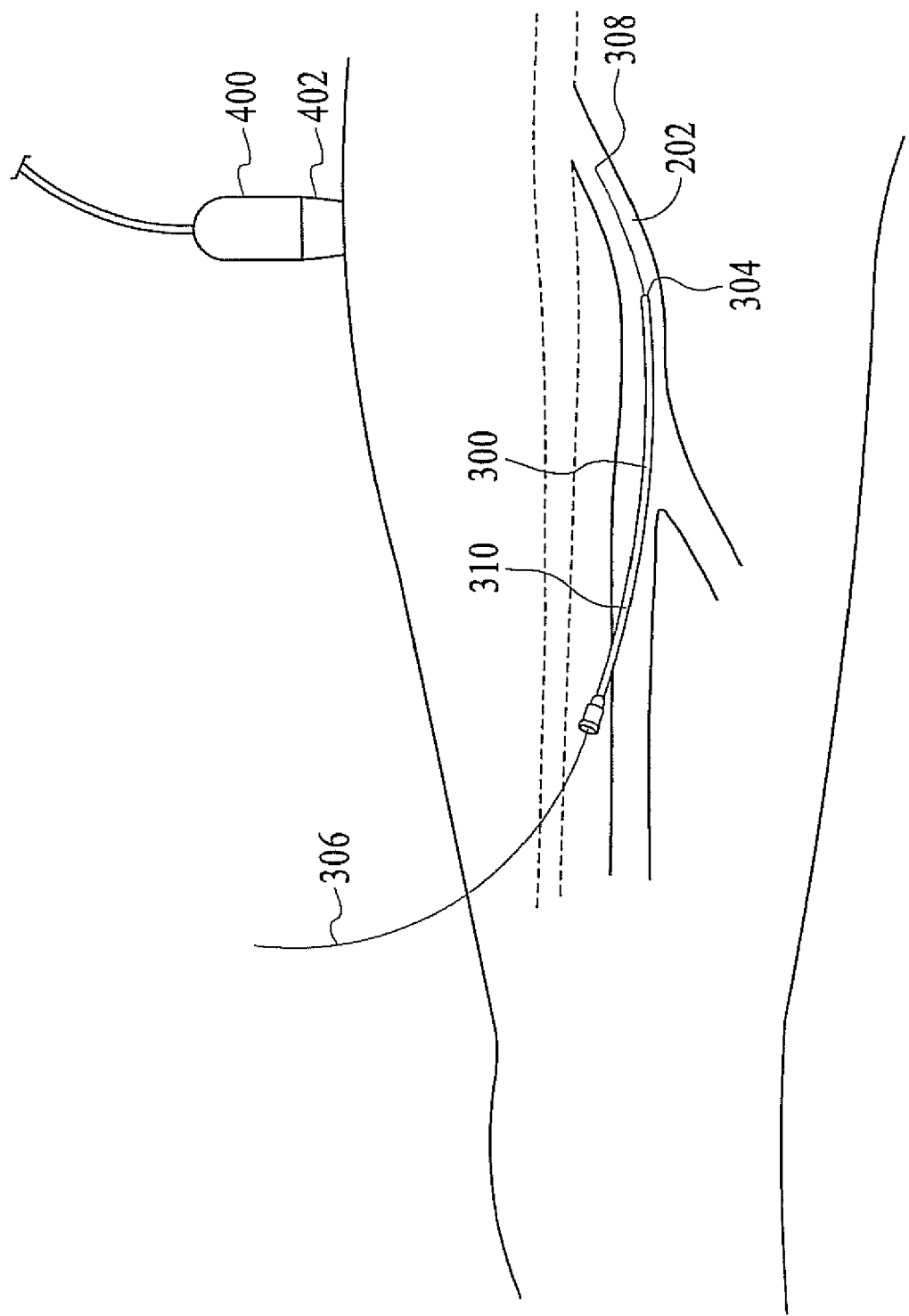
FIG. 4 is a representative view of the use of an ultrasound device 400 according to the method and apparatus of the present invention.
Figure 5:
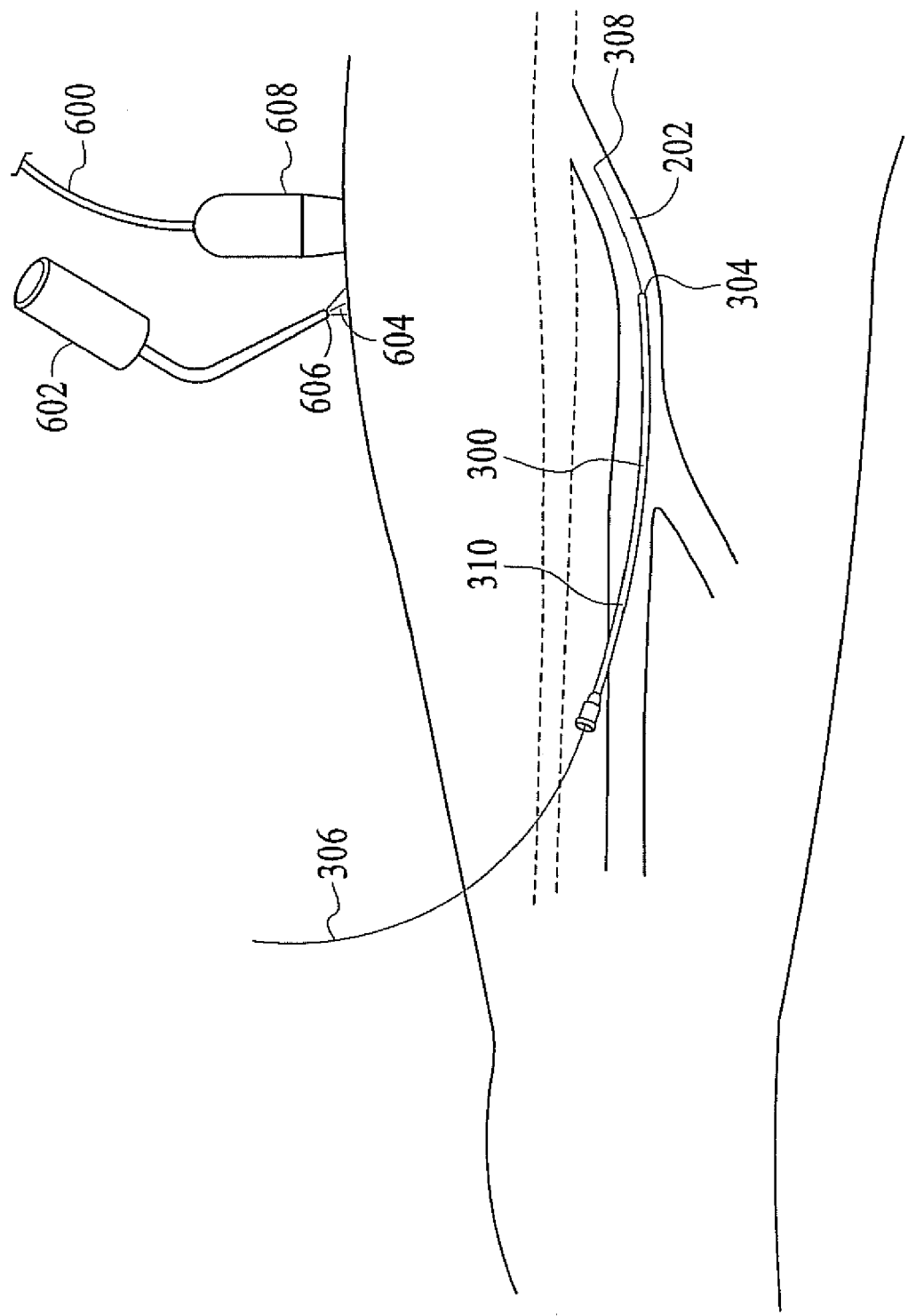
FIG. 5 is a representative view of the non-contact thermal sensor 600 and the cooling system 602 of the method and apparatus of the present invention.

FIG. 4 is a representative view of the use of an ultrasound device 400 according to A method and apparatus of the present invention. FIG. 5 is a representative view of a physician 500 performing manual compression of tissue near the tip 308 of the fiber 306 according to the method and apparatus of the present invention. As described herein, it will be understood that the means for applying mechanical compression of the tissue near the tip 308 of the fiber includes manual compression, mechanical clamps or straps, chemical or other drug-induced swelling, etc.

FIG. 5 is a representative view of the non-contact thermal sensor 600 and the cooling system 602 of the method and apparatus of the present invention. Non-contact thermal sensors 600 as well as contact devices, including RTDs, are well known in the art. It will be understood that the cooling device 602 can be any suitable, controlled device which allows a predetermined amount of cryogenic fluid to be dispensed from an on-board fluid reservoir or from an external/line source. In a preferred embodiment, the device 602 is computer controlled, to provide spurts or squirts of cryogenic fluid at a predetermined rate or for a predetermined duration. The cryogenic fluid is dispensed onto the surface of the skin 604 in an area adjacent the fluid dispensing nozzle 606, and the non-contact thermal sensor 600 determines the temperature of the skin in the same area 604 or in an area 608 distal from the area being cooled 604. The present invention, this application and any issued patent based hereon incorporates by reference the following issued patents with regards surface cooling methods and apparatus utilized in the present invention: U.S. patent application Ser. No. 08/692,929 filed Jul. 30, 1996, now U.S. Pat. No. 5,820,626. U.S. patent application Ser. No. 08/938,923 filed Sep. 26, 1997, now U.S. Pat. No. 5,976,123. U.S. patent application Ser. No. 10/185,490 filed Nov. 3, 1998, now U.S. Pat. No. 6,413,253. U.S. patent application Ser. No. 09/364,275 filed Jul. 29, 1999, now U.S. Pat. No. 6,451,007.

Figure 6:
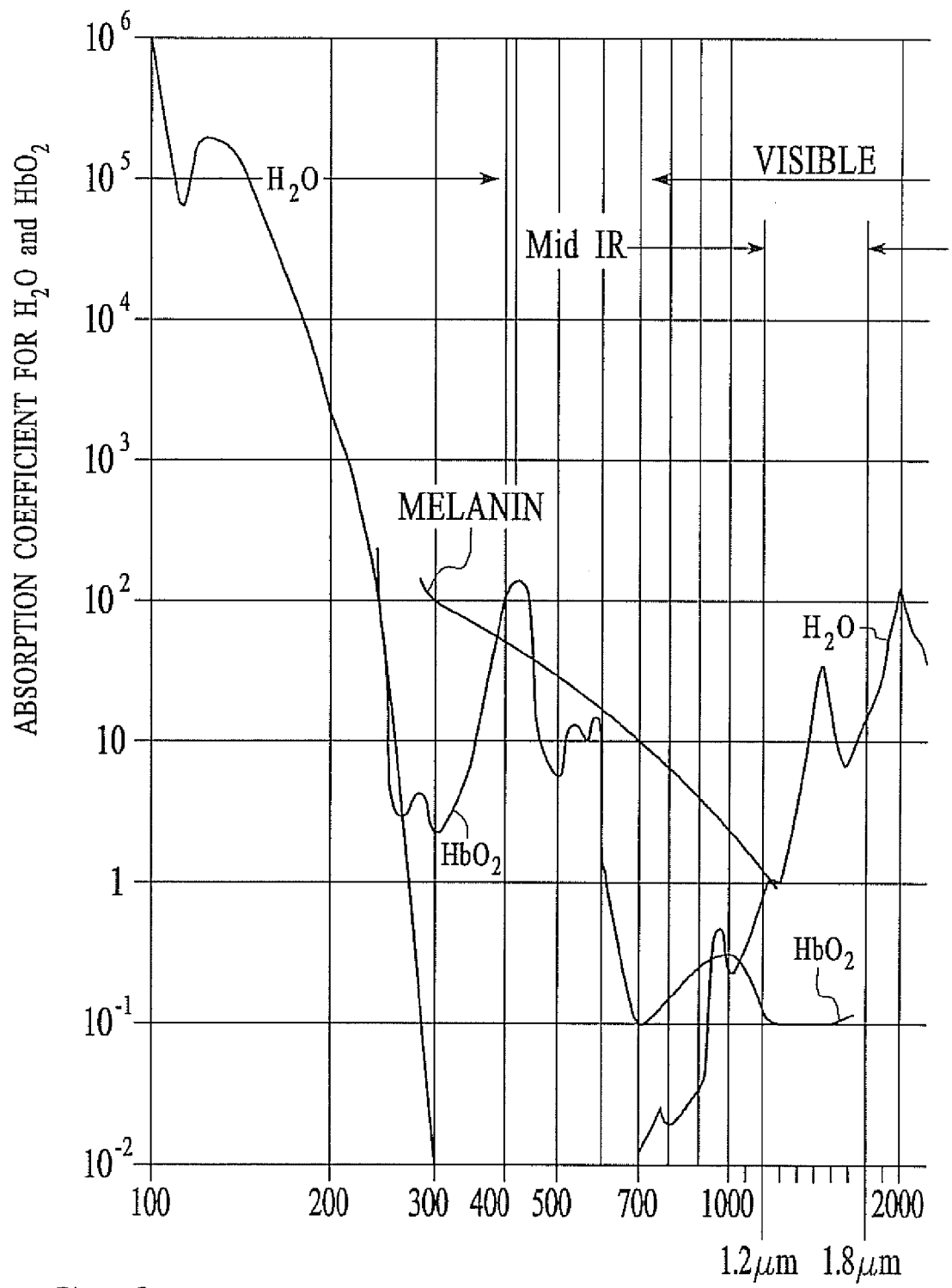
FIG. 6 shows curves for absorption coefficients of melanin, hemoglobin and water as a function of wavelength according to the method and apparatus of the present invention.

FIG. 6 shows curves for absorption coefficients of melanin, hemoglobin and water as a function of wavelength according to the method and apparatus of the present invention. It will be observed in FIG. 6 that the region between about 550 nm to about 1060 nm shows high hemoglobin absorption and low water absorption, as is well known in the prior art technology. It will further be observed that the region between about 1200 nm to about 1800 nm shows low hemoglobin and higher water absorption, which is a key to the present invention.

Clinical Results:

The following is a description of a study undertaken with the financial support of the American College of Phlebology BSN-JOBST Phlebology 2006 Research Grant.

Our results were presented at the 20th Annual Congress of the American College of Phlebology at Sawgrass Marriott Resort and Beach Club, Ponte Vedra Beach, Fla., Nov. 9-12, 2006.

Objective Summary:

Venous disease was proposed as a cause of Restless Legs Syndrome (RLS) by Dr. Karl A. Ekbom in 1944, but has since remained largely unexplored. This study examines the effect of Endovenous Laser Ablation (ELA) in patients with concurrent RLS and duplex-proven Superficial Venous Insufficiency (SVI) The aim of this study is to determine what effect ELA has in patients with RLS and SVI.

Methods Summary:

Thirty-five patients with moderate to very severe RLS (as defined by the 2003 NIH RLS criteria) and duplex-proven SVI completed an International RLS rating scale questionnaire (IRLS) and underwent standard duplex examination to objectively measure the baseline severity of their conditions. They were separated into non-operative and operative cohorts. The operative cohort underwent ELA of refluxing superficial axial veins using the CoolTouch CTEV 1320 nm laser and ultrasound-guided sclerotherapy of the associated varicose veins with foamed sodium tetradecyl sulfate (STS). All patients then completed a follow-up IRLS questionnaire. Baseline and follow-up IRLS scores were compared.

Results Summary:

Operative correction of the SVI decreased the mean IRLS score by 21.4 points from 26.9 to 5.5, corresponding to an average 80% improvement in symptoms. Eighty-nine percent of patients enjoyed a decrease in their score of $\geq 15$ points. Fifty-three percent of patients had a follow-up score of $\leq 5$, indicating their symptoms had been largely alleviated, and 31% had a follow-up score of zero, indicating complete relief of RLS symptoms.

Conclusions and Recommendations Summary:

ELA of refluxing axial veins with the CTEV 1320 nm laser and foamed STS sclerotherapy of associated varicosities alleviates RLS symptoms in patients with SVI and moderate to very severe RLS. Additionally, SVI should be ruled out in all patients with RLS before initiation or continuation of drug therapy.

Patients and Study Design:

We screened 89 patients with complaints of restlessness in their legs. The diagnosis of RLS was determined using the 2003 NIH criteria. All patients who met the criteria for RLS were interviewed to confirm the diagnosis of RLS and to exclude conditions that mimic RLS (such as positional discomfort, neuropathy, night cramps, etc.). They then completed an initial IRLS questionnaire to determine the baseline severity of their disease. Those patients with an IRLS score of 15 or greater (corresponding with moderate to very severe RLS) underwent a screening duplex ultrasound. Patients found to have greater than 500 milliseconds of reflux in the great saphenous vein (GSV) underwent a complete duplex evaluation of the deep, superficial, and perforator systems. All reflux was mapped for appropriate treatment. Thirty-five patients met the criteria and were accepted into the study.

Sixteen patients were assigned to the non-operative cohort, 19 to the operative cohort. In the non-operative cohort 6.3% of patients were male and 93.7% were female. The mean age was 58.8, and the average weight 180.2 pounds. In the operative cohort, 31.6% of patients were male and 68.4% were female. The mean age was 49.4, and the average weight was 202.5 pounds. One patient withdrew from each cohort for unrelated medical reasons.

Most RLS patients take medication nightly in order to get some sleep. We felt it important for this study to be applicable to the broader population. We therefore did not exclude patients who were taking RLS medications. In order to stabilize RLS medication as a variable, we did ask patients not to add any or discontinue medications known to affect RLS symptoms during the study period.

Intervention:

Patients were assigned to either the non-operative or operative cohort. Non-operative patients completed a follow-up questionnaire six weeks after the initial questionnaire. This yielded objective measurements of the severity of the baseline and final RLS symptoms in the non-operative cohort.

The operative patients underwent ELA of all refluxing axial veins using the Cool-Touch 1320 nm laser at settings of 50 Hz and 7 Watts. The pullback device was set on 0.5 mm/sec for the first 10 cm, then 1.0 mm/sec for the remainder of the vein. These laser settings applied 140 Joules/cm to the first 10 cm of vein, and 70 Joules/cm to the remainder of the vein (this rather high fluence was utilized to ensure 100% ablation of all treated veins). Varicose veins and refluxing perforator veins were treated with ultrasound-guided sclerotherapy using 1.0% STS foam. A 6-inch ACE wrap was applied immediately post-operatively and continued for 48 hours, then replaced with 20-30 mm/hg compression stockings for two weeks. Compression was then removed. Operative patients underwent a post-operative duplex examination 2-3 days after the procedure, and again six weeks later. They completed a final IRLS questionnaire at the 6-week follow-up appointment. The baseline and final IRLS scores of both groups were then compared.

Study Design and Statistical Analysis:

The 35 patients who met the inclusion criteria were enrolled into this prospective, randomized, unblinded, parallel two-group, pre-post-test study. This study design involved outcome variables measured on binomial and continuous scales. For the continuous outcome variables (i.e., IRLS questionnaire), one-way analysis of variance with two distinct levels of the intervention was performed. Moreover, since unequal sample sizes were anticipated and observations were repeated over time, Bonferroni procedures were appropriate to control for experimentwise, multi-comparison error. Matched-pairs analysis was used to test the null hypothesis of zero change from IRLS baseline score.

When analyzing binomial variables (i.e., RLS Symptoms Alleviated, yes or no), Chi-square and likelihood ratio statistics were computed to test the null hypothesis of no association between the intervention groups and the response variable(s). In addition, since single-group pre- and post-test comparisons were performed and the assumption of independent samples was not met, McNemar's test for matched pairs was appropriate. Exact tests were used and exact probabilities were computed where appropriate.

All statistical analysis activities were performed using SAS Statistical Software, Version 9.1.3, SAS Institute, Inc., North Carolina, USA. The procedures used are PROC ANOVA, PROC GLM, and PROC FREQ.

Results:

Duplex evaluation performed 6 weeks postoperatively revealed that 100% of the treated veins were successfully ablated. Transient postoperative discomfort in the region of the treated veins was frequently reported. Most patients required only PRN Ibuprofen, foregoing the prescribed hydrocodone. All patients had mild bruising at the access sites. There were no major side effects or complications.

When comparing mean baseline IRLS scores for the non-operative and operative cohorts, 26.8 vs. 26.9 respectively, the difference was not found to be statistically significant ($p=0.971$). Consequently, one could assume homogeneity in RLS symptoms and severity across treatment groups prior to intervention. At the final evaluation, the mean IRLS score in the non-operative cohort was actually found to be slightly elevated (28.4) in contrast to their baseline mean score. The mean IRLS score in the operative cohort decreased by 21.4 points to 5.5. This represents a drop in symptom severity of 80%. The matched-pairs analysis was statistically significant ($p<0.0001$) indicating that the change from baseline in IRLS score for the operative group was significantly greater than the change from baseline in IRLS score for the non-operative group.

Eighty-nine percent of operative patients enjoyed a decrease in their IRLS score of 15 points or more. Seventy-nine percent of patients improved to "mild" disease (final score$\leqq$10). Ninety-five percent of patients improved to "mild" or "moderate" disease (final score$\leqq$20). Fifty-three percent of patients had a final score$\leqq$5, indicating their RLS symptoms had been largely alleviated. Thirty-one percent of patients had a final score of zero, indicating complete relief of RLS symptoms.

Discussion:

In Dr. K. A. Ekbom's original 1944 article, he presented 8 patients with what he called asthenia crurum paraesthetica "irritable legs". He described the symptoms RLS and said that, in most patients, objective signs were lacking. One (12.5%) of these patients, however, was noted to have varicose veins. Dr. Ekbom went on to say that all patients had palpable dorsalis pedis pulses, yet he concluded "It is possible that the condition is due to a functional vascular disorder." He suspected venous congestion and an accumulation of metabolites to be a cause of RLS. Our study demonstrates that treating the underlying venous disease can relieve the RLS symptoms.

Venous insufficiency is an impedance of venous flow back to the heart. It is usually caused by venous reflux secondary to valvular failure and can occur in the deep, superficial, or perforator veins. Venous insufficiency results in high venous pressures that are transmitted to tributary veins, venules, capillaries and interstitial tissues drained by the diseased vein. It affects 10-15% of men and 20-25% of women. SVI is much more common than deep venous insufficiency.

According to the Starling concept, most of the fluid forced out of the capillary bed at the arterial end is normally returned into the lumen at the venous end. In tissues affected by venous hypertension, this delicate balance is disrupted. The high hydrostatic pressure in the venules and capillaries causes a net increase in the fluid remaining in the interstitial space. This increased interstitial fluid volume overwhelms the lymphatic capacity, resulting in edema formation. As long as the leg is dependant, the interstitial fluid continues to accumulate, until the tissue pressure rises to a point at which the Starling equilibrium is restored. Considerable edema can accumulate before this point of equilibrium is reached. Upon elevation of the leg (such as when the patient is lying down or reclining), the venous pressures diminish and the lymphatics can drain the engorged interstitium.

The circadian ebb and flow of edema fluid seen in venous insufficiency closely parallels the circadian timing of RLS symptoms. This is more than mere coincidence. We know that the daily accumulation of soft tissue edema creates unpleasant sensations in the legs such as heaviness, fullness, achiness, etc. The nightly receding of that edema fluid somehow causes the "indescribable" sensations that typically plague RLS patients. This would explain why the typical RLS symptoms occur when the patient is reclining and at night, as the elevation mobilizes edema from the legs, and why symptoms seem to wane in the early morning hours (the edema has largely resolved by that time. The restless leg movement is a subconscious activation of the musculovenous pump, stretching of afflicted muscles and tendons, or a distractor to mask the tormenting sensations.

This discovery is supported by the fact that 26% of women are affected by RLS during their pregnancy. Pregnancy has been shown to exacerbate both RLS and edema independently. Strong correlation is noted with the third trimester of pregnancy (when the pregnancy-associated edema is at its peak) and tends to disappear with delivery (when the pregnancy-associated edema has receded).

Similar findings are seen in hemodialysis patients. RLS affects 20-80% of this population. Despite extensive research of various clinical and biochemical parameters, the cause of RLS in this population remains unknown. It has been shown that increasing dialysis from 3 days a week to 5 days a week (but not changing total number of hours per week) relieves the RLS symptoms. RLS symptoms disappear in hemodialysis patients who receive a kidney transplant. Frequent dialysis dampens and renal transplant eliminates the huge volume swings normally seen in hemodialysis patients, thus impacting their RLS symptoms.

Primary RLS is generally felt to be a condition in which an abnormal nervous system is reacting inappropriately to relatively normal legs. In RLS patients with venous disease, it appears that RLS is due to a relatively normal nervous system reacting appropriately to abnormal legs.

Strengths and Limitations of the Study:

We employed the NIH criteria to make the diagnosis of RLS and the IRLS questionnaire to grade the severity of symptoms. These tools are widely utilized in current RLS research. They made possible accurate comparisons between operative and control groups. This allowed us to gather statistically significant results despite our small sample size.

Bias was introduced in this study by including only those RLS patients with duplex-proven SVI. All RLS patients with normal venous function were therefore excluded. Bias was also introduced in the manner in which the patients were assigned to operative vs. nonoperative cohorts. Medicare and third party insurance carriers require a three to six month trial of "conservative non-operative measures". Because of time constraints, patients who had not met these criteria before presenting to our vein center were automatically placed in the non-operative cohort. Patients who had met these mandates were placed in the operative cohort. Further study will explore the connections between RLS, venous insufficiency, and lower extremity edema.

CONCLUSIONS

Our results demonstrate that ELA of refluxing axial veins and sclerotherapy of associated varicosities alleviates or relieves RLS symptoms in patients with moderate to very severe RLS and SVI. All RLS patients should be properly evaluated for venous insufficiency by a technician familiar with techniques to detect venous reflux before initiation or continuation of drug therapy. Any RLS patient with venous insufficiency should be referred for evaluation and treatment by a phlebologist. Following these methods and procedures, these patients can escape the nightly torment of chronic RLS.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, one methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. A method for treatment of restless leg syndrome in a patient with reflux in a leg vein, the method comprising the following steps:
    A. Performing an exam of veins contributing to vascular insufficiency and reflux;
    B. Obtaining percutaneous access of the vessel being treated using a Seldinger or equivalent technique;
    C. Advancing a catheter with catheter tip through an introducer sheath until it is approximately 1-2 cm below the saphenofemoral junction (SFJ) or the saphenopopliteal junction (SPJ) or at the appropriate distance based on the junction or vein being treated;
    D. Confirming position of the catheter tip such as with ultrasound, aiming beam visualization, or equivalent;
    E. Draining blood from the vein using elevation, suction, compression, vein spasm, or other technique;
    F. Injecting local anesthesia around the vein being treated; and
    G. Initiating treatment with a device which emits a diode laser or other laser source, electrical current, radiofrequency waves, microwaves, ultrasound or other source of electromagnetic energy which penetrates into regions of tissue.

2. The method of claim 1 further comprising the step of increasing wattage of energy delivered to tissue as desired.

3. The method of claim 1 further comprising the step of determining endpoint of treatment by observing indications of adequate tissue response, such as slowing or stopping of forward movement of flow, thickening of the vein wall, contracting of the vein, and decreasing size of the lumen of the vein.

4. The method of claim 1 further comprising the step of determining successful treatment by observing, such as with ultrasound, following treatment, any one of the group consisting of vein appearing more dense and thickened (more echogenic), vein less compressible with pressure from the ultrasound probe, vein lumen is noticeably smaller in size, and vein does not demonstrate spontaneous flow.

* * * * *